United States Patent [19]

Cordes et al.

[11] Patent Number: 4,879,234
[45] Date of Patent: Nov. 7, 1989

[54] PROCESS FOR THE PURIFICATION AND RECOVERY OF FORMATE-DEHYDROGENASE (FDH) FROM *CANDIDA BOIDINII*, AND FDH-CONTAINING PRODUCT

[75] Inventors: Arno Cordes, Salzgitter; Maria-Regina Kula, Niederzier-Hambach; Karl-Heinz Kroner, Wolfenbüttel; Wolfgang Stach, Salzgitter, all of Fed. Rep. of Germany

[73] Assignee: Gesellschaft fur Biotechnologische Forschung mbH (GBF), Braunschweig, Fed. Rep. of Germany

[21] Appl. No.: 891,868

[22] Filed: Jul. 30, 1986

[30] Foreign Application Priority Data

Jul. 30, 1985 [DE] Fed. Rep. of Germany ....... 3527268

[51] Int. Cl.$^4$ ............................ C12N 9/02; C12R 1/72
[52] U.S. Cl. .................................. 435/189; 435/183; 435/188; 435/921
[58] Field of Search ................. 435/183, 189, 921, 188

[56] References Cited

U.S. PATENT DOCUMENTS 3,133,001  5/1964  Muset ................................... 435/188
4,229,529 10/1980  Michal et al. ......................... 435/26

FOREIGN PATENT DOCUMENTS

WO84/04309 11/1984 PCT Int'l Appl. ................. 435/183

OTHER PUBLICATIONS

Watson, David H., Michael J. Harvey and Peter D. G. Dean, "The Selective Retardation of NADP-+-Dependent Dehydrogenases by Immobilized Procion Red HE-3B", Biochem. J., vol. 173 (1978), pp. 591–596.

Kroner, K. H., H. Husteadt, & M. R. Kula, "Evaluation of Crude Dextran as Phase-Forming Polymer for the Extraction of Enzymes in Aqueous Two Phase Systems in Large Scale", Biotechnology & Bioengineering, vol. 24 (1982), pp. 1015–1045.

Kroner, K. H., H. Hustedt, S. Granda, & M. R. Kula, "Technical Aspects of Separation Using Aqueous Two-Phase Systems in Enzyme Isolation Processes", Biotech & Bioengineering, vol. 20 (1978), pp. 1967–1988.

Kroner, K. H., H. Schütte, W. Stach & M. R. Kula, "Scale-Up of Formate Dehydrogenase by Partition", J. Chem. Tech. Biotechnol., vol. 32 (1982), pp. 130–137.

Hustedt, H., K. H. Kroner, W. Stach, & M. R. Kula, "Procedure for the Simultaneous Large-Scale Isolation of Pullulanase and 1,4-α-Glucan Phosphorylase from *Klebsiella pneumoniae* Involving Liquid-Liquid Separation", Biotech & Bioengineering, vol. 20 (1978) pp. 1988–2005.

Primary Examiner—Robert A. Wax
Attorney, Agent, or Firm—Kane, Dalsimer, Sullivan, Kurucz, Levy, Eisele and Richard

[57] ABSTRACT

The invention relates to a process for the purification and, if desired, recovery of formate-dehydrogenase (FDH) from *Candida boidinii*, in which FDH is subjected to a phase distribution in an aqueous 2-phase system that contains a triazine dyestuff that is bonded to an inert water-soluble polymer.

14 Claims, No Drawings

PROCESS FOR THE PURIFICATION AND RECOVERY OF FORMATE-DEHYDROGENASE (FDH) FROM CANDIDA BOIDINII, AND FDH-CONTAINING PRODUCT

BACKGROUND OF THE INVENTION

1. Field of the Invention

The invention relates to a process for the purification and recovery of formate-dehydrogenase from *Candida boidinii*

2. Brief Description of the Prior Art

Formate-dehydrogenase (FDH) is present intracellularly in *Candida boidinii*. Hitherto two different processes have been used to recover FDH. Thus, in Eur. J. Biochem., 62 (1976), 151–160 a process is described in which *Candida boidinii* is cultured, the harvested cells are frozen, left to stand in an aqueous phosphate-containing medium and then mechanically disintegrated, the cell debris is centrifuged off, residual protein is precipitated with Streptomycin sulphate and the precipitate is centrifuged off, after which the supernatant solution is subjected to ion-exchange chromatography on DEAE cellulose to recover the enzyme. There is also known, from J. Chem. Tech. Biotechnol., 32 (1982) 130 to 137, a process in which *Candida boidinii* is cultured, the harvested cells are mechanically disintegrated, the resulting cell suspension is subjected to heat-denaturation and the resulting suspension is subjected to four successive phase distribution steps, using aqueous 2-phase systems with polyethylene glycol and potassium phosphate as phase formers.

In addition, a series of papers on the affinity distribution of non-intracellular enzymes in phase systems containing triazine dyestuffs that are bonded to polyethylene glycol have been disclosed; cf., for example, Kroner et al. in Gribnau et al., Affinity chromatography and related techniques, [pages 491 to 501], Elsevier, Amsterdam 1982; Cordes et al. in Publ. 3rd Eur. Congr. Biotechnology, Munich 1984, Vol III, pages 557 to 564; Eur. J. Biochem., 131 (1983) 589 to 594; J. Chromatography, 259 (1983) 97 to 105; Analytical Biochemistry, 136 (1984) 264 to 271; and J. Chromatography, 298 (1984) 483 to 493. Finally, in Analytical Biochemistry, 124 (1982) 117 to 124 a process is described in which baker's yeast is used as the starting material, and phosphofructokinase, used as the non-intracellular enzyme, is precipitated with polyethylene glycol and subsequently subjected to a phase distribution in an aqueous 2-phase system, the system comprising dextran, polyethylene glycol and Cibacron-blue-S3G-A as the triazine dyestuff that is bonded to polyethylene glycol.

With the known processes for the purification and, if desired, recovery of FDH there is a need, however, to reduce the number of purification steps.

SUMMARY OF THE INVENTION

To this end, in accordance with the invention a process is provided for the purification and, if desired, recovery of formate-dehydrogenase (FDH) in which (a) the enzyme-containing cells are disintegrated, (b) the cell material together with the cell liquid is subjected to a phase distribution (affinity extraction), (c) the enzyme is, if desired, separated from the enzyme-rich phase and, if desired, recovered, this process being characterised in that in step (b)

if desired without previous separation of the cell material and if desired without previous separation of foreign protein the phase distribution is carried out with an aqueous 2-phase system in one phase of which there is concentrated a triazine dyestuff that is bonded to polyethylene glycol or polypropylene glycol.

In accordance with the invention it has therefore surprisingly been found that FDH can be purified without previous separation of cell material and foreign protein if FDH is subjected to a phase distribution in an aqueous 2-phase system that includes a triazine dyestuff that is bonded to an inert water-soluble polymer.

DETAILED DESCRIPTION OF THE PREFERRED EMBODIMENTS OF THE INVENTION

In one embodiment of the process according to the invention, the *Candida boidinii* cells, after having previously been frozen, are suspended in an aqueous phosphate-containing medium and left in suspension until an enzyme efflux of a maximum of approximately 90, 85 or 75% has occurred, after which the resulting suspension is subjected to the phase distribution. The phosphate-containing medium may contain potassium phosphate and/or potassium hydrogen phosphate ($K_2HPO_4$ and/or $KH_2PO_4$). Disintegration of the *Candida-boidinii* cells is not necessary. This embodiment of the invention is based on the observation that, after freezing the cells and suspending them in an aqueous phosphate-containing medium, FDH diffuses out first and almost completely, whereas a large proportion of the residual protein still remains in the cells.

The medium resulting after an enzyme efflux of a maximum of approximately 95, 85 or 75% can also be a starting material for another FDH recovery process, that is to say, the medium does not have to be used for the phase distribution according to the invention.

According to a further embodiment of the process according to the invention, the suspension of disintegrated cells can be heated and then cooled again. As a result some proteins are coagulated and can then easily be removed with the cell material. Furthermore, heat-labile proteins, such as dehydrogenases or kinases, are deactivated, so that they cannot enter into any bond with the ligand.

Preferably, there is used an aqueous 2-phase system with (a) polyethylene glycol or polypropylene glycol and (b) crude dextran, dextran, methylcellulose or Ficoll as phase former. Otherwise, it is left to the person skilled in the art to select suitable 2-phase systems, cf., for example, DE-C-26 39 129.7 and the Literature listed therein.

Examples of triazine dyestuffs are:

Procion Yellow H-5G (C.I. 18972)

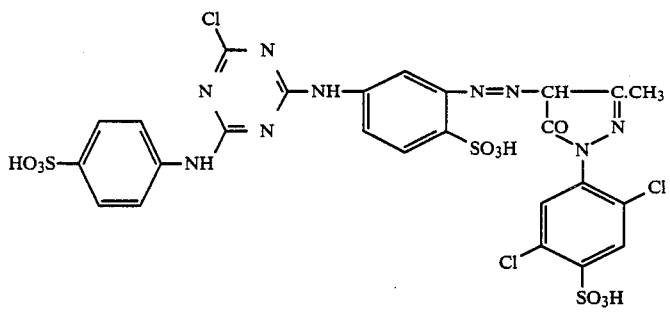
Procion Yellow H-A  (C.I. 13245)
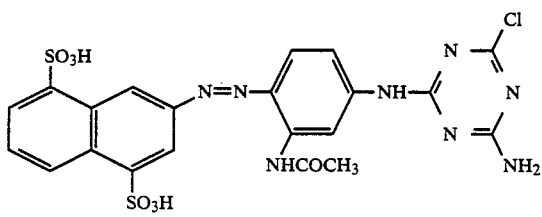
Procion Brown H-2G  (C.I. 26440)
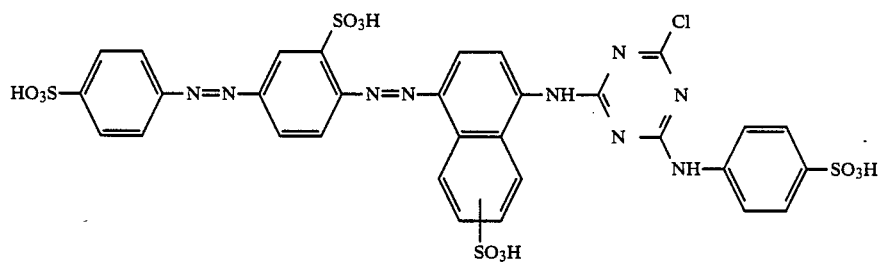
Procion Red H-3B  (C.I. 18159)
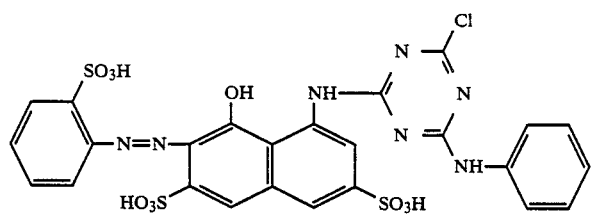
Procion Blue H-B  (C.I. 61211)
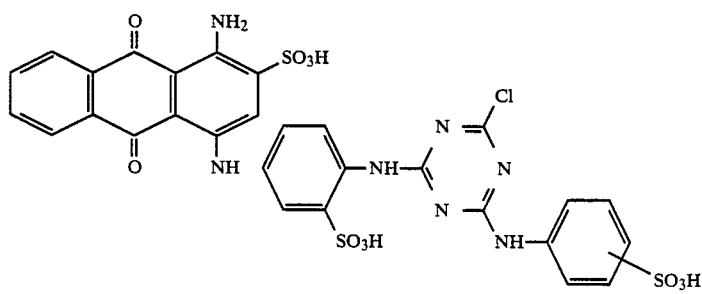
Procion Yellow MX-6G  (C.I. 18971)

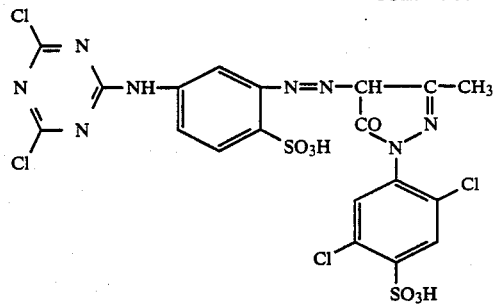
Procion Yellow MX-R (C.I. 13190)
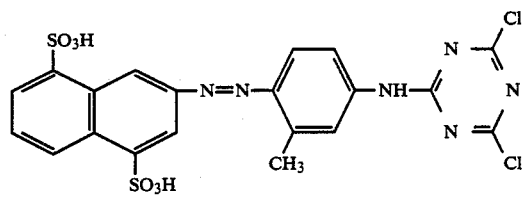
Procion Red MX-2B (C.I. 18158)
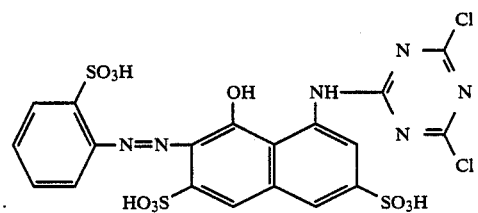
Procion Rubine MX-B (C.I. 17965)
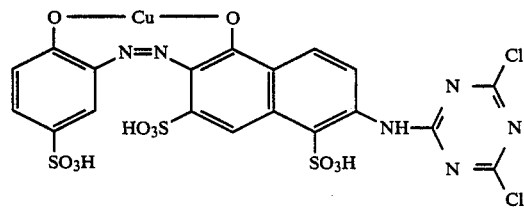
Procion Scarlet MX-G (C.I. 17908)
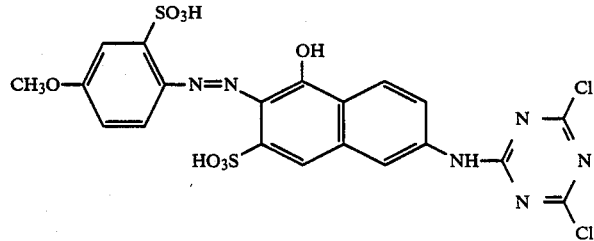
Procion Blue MX-R (C.I. 61205)
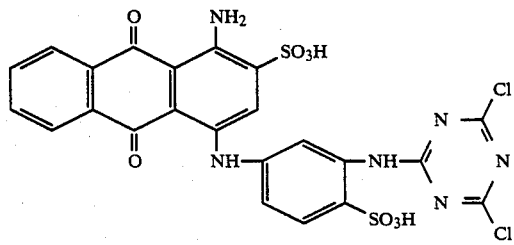

-continued
Procion Orange MX-G
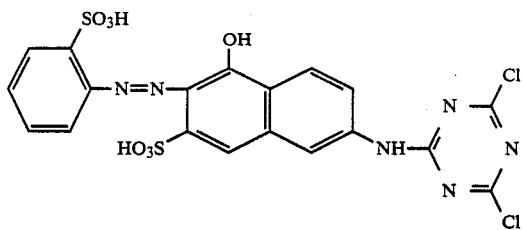
Procion Red MX-5B
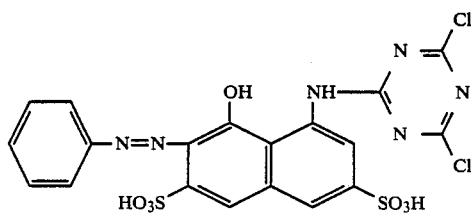
Procion Blue MX-3G
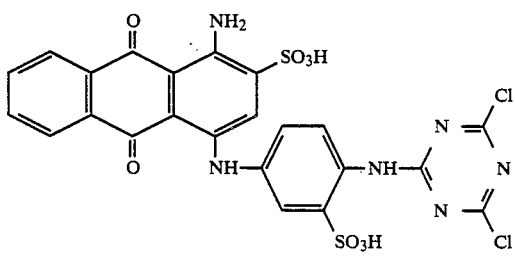
Procion Orange H-GR
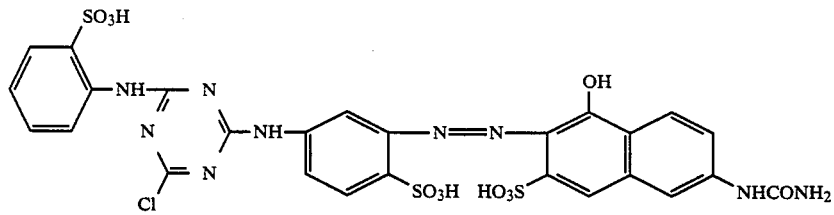
Procion Green MX
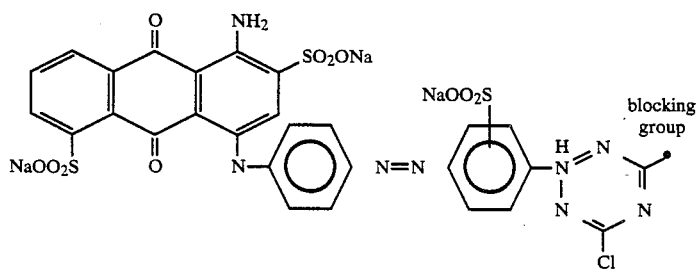
Structural formula of the dyestuff
Cibacron blue 3GA

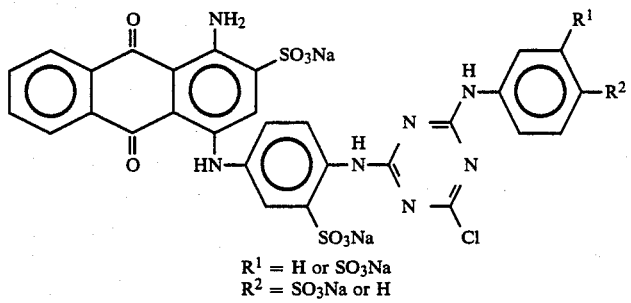

R$^1$ = H or SO$_3$Na
R$^2$ = SO$_3$Na or H

Structural formula of the dyestuff
Procion red HE3B

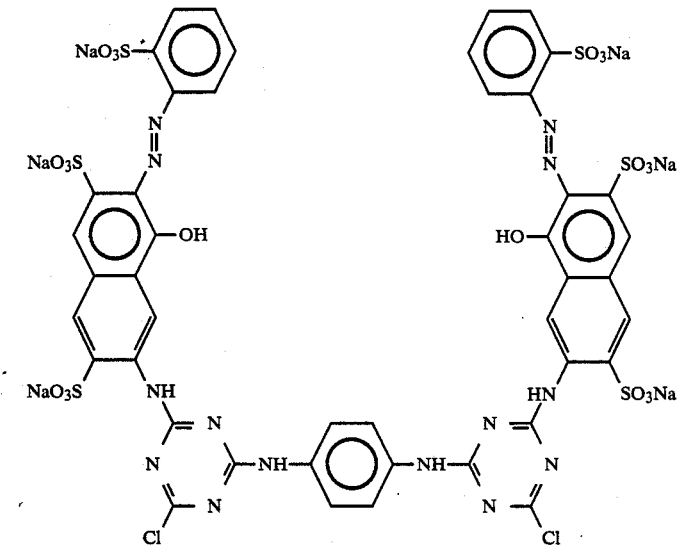

Procion-red-HE3b is especially suitable. To link triazine dyestuffs with an inert water-soluble polymer, reference is made, for example, to Analytical Biochemistry 124 (1982) 117 to 124, and the following Method 1. The information to be found in the two references given can be applied to other inert water-soluble polymers.

The invention relates also to a process in which, with an aqueous 2-phase system with
(a) polyethylene glycol or polypropylene glycol and
(b) crude dextran, dextran, methylcellulose or Ficoll as phase formers, and a triazine dyestuff (such as Procion-red-HE3b) bonded to polyethylene glycol or polypropylene glycol as ligand,
the upper phase containing the concentrated enzyme is separated from the lower phase and a salt, especially potassium phosphate and/or potassium hydrogen phosphate, is added thereto, and the enzyme is conveyed into the lower phase of the resulting 2-phase system and, if desired, separated (especially by ultrafiltration) from the salts and phase formers.

Preferably, the ligand-containing upper phase is used again and preferably polyethylene glycol or polypropylene glycol is added to the lower phase into which the enzyme has been conveyed, and the upper phase of the resulting 2-phase system is combined with the previously separated upper phase and then used again.

It is advantageous to lyophilise the enzyme present in a liquid medium free of phase formers and salts in the presence of saccharose, since the resulting product is stable to storage. The invention relates lastly to this formate-dehydrogenase-containing solid product having a content of saccharose.

The invention is explained in more detail in the following:

METHOD 1

Step 1: Chlorination. Monomethoxy-polyethylene glycol (MPEG) or polyethylene glycol (PEG) with, for example, a molecular weight of 400, 1,500, 4,000, 6,000 or 10,000 (abbreviated in the following to PEG), is used as starting material. Solid PEG or MPEG is melted at 70° C. overnight in a drying chamber. The optionally molten PEG or MPEG is then freed from water in vacuo. The chlorination is carried out in a rotary evaporator at 70° C. with a 50 molar excess of thionyl chloride. Since the operation must be carried out absolutely water-free because of the risk of HCl formation, the reaction vessel is gassed with nitrogen and a drying tube is mounted on the condenser. After approximately 8 hours the reaction is complete. The excess thionyl chloride is removed in vacuo.

Step 2: Amination. The chlorinated PEG or MPEG is dissolved in a large excess of aqueous ammonia (25%) in a glass autoclave (1.5 l). The reaction vessel should be approximately ¾ full; it is then sealed air-tight. Subsequently, amination is carried out in an oil bath at 110° C. for approximately 30 h. The reaction product is concentrated in a rotary evaporator, the excess ammonia being removed.

Step 3: Coupling. 1 molar Procion-red-HE3b is added to 1 molar NH₂. The pH is subsequently adjusted to 11 and the reaction is carried out for approximately 24 hours at 60° C. The reaction product is subjected to gel filtration (Sephadex-G50) in order to separate the free dyestuff, and is subsequently dialysed.

EXAMPLE 1

Step 1: Suspension. 10 kg of frozen yeast are suspended in a potassium phosphate buffer overnight using a propeller-stirrer. The solution contains 40% cell mass, 10% ammonium formate and 0.1M potassium phosphate. The volume is 25 l. Next morning the enzyme activity is measured.

Step 2: Heat-denaturation. The cell suspension is heated in a water bath (75° C.) and maintained at 60° C. while stirring. The temperature is monitored with a thermometer in the reaction vessel. The heating up time amounts to approximately 15 mins. After approximately 10 mins. at 60° C., the cell suspension is cooled to room temperature in ice-water.

Step 3: Affinity distribution. For this the following are weighed out:

| | |
|---|---|
| 9% PEG10000 (reduced by the proportion of PEG-red) (polyethylene glycol with a mean molecular weight of 10,000) | 4.356 kg |
| 43 mmol MPEG-red (Procion-red-HE3b bonded to monomethoxy-polyethylene glycol having a mean molecular weight of 5,000; as an aqueous solution) | 1.240 kg |
| 1% crude dextran (10% solution) | 0.500 kg |
| 25 l 40% cell suspension (density = 1.076 kg/l) | 26.900 kg |
| Water ad 50-kg. | |

The system is mixed thoroughly for 30 mins. with a blade stirrer. Care must be taken in doing this that there is no pronounced foam formation. Then, the system is separated in a nozzle separator (4 nozzles with a diameter of 0.4 mm) at a flow rate of 500 ml/min. The purity of the phases is 95% for the upper phase and 90% for the lower phase. The gelatinous lower phase is discarded.

Step 4: Separation of enzyme-ligand. The upper phase (38.57 l) is mixed with 9% potassium phosphate (weight/volume; system: 10.5% PEG10,000/9.9% potassium phosphate); after dissolution of the salt stirring is carried out for a further 10 minutes and then separation is carried out at a flow rate of 400 ml/min in a disk separator (nozzle length 14.5 mm). The purity of both phases is of the order of 100%. The upper phase is kept at −20° C. for further use. The lower phase is mixed with 1% PEG10,000 and, after dissolution thereof, is again separated at 400 ml/min in the separator. The upper phase is stored with the upper phase of the first PEG/salt system.

Step 5: Ultrafiltration. The lower phase (27.3 l) is freed of salts and polyethylene glycol in a capillary membrane system (filtrate throughput 50 l/h), and concentrated to a volume of 5.28 l. Subsequently, concentration is carried out in a second capillary membrane apparatus to produce a final volume of 1 l.

Step 6: Lyophilisation. 171 g of saccharose are added to the material retained on ultrafiltration. Lyophilisation is then carried out in a freeze-drier. 243 g of product of an activity of 0.23 U FDH/mg lyophilisate are obtained.

EXAMPLE 2

Example 1 is repeated except that instead of 43 mmol MPEG-red an aqueous solution with a content of 400 mmol MPEG-blue (Cibacron-blue-3G-A bonded to monomethoxypolyethylene glycol) is used. A lower specific activity and yield are obtained by comparison with Example 1.

We claim:

1. Process for the purification and recovery of formate-dehydrogenase enzyme from *Candida boidinii* cells, which comprises:
   (a) disintegrating the enzyme-containing cells to obtain a mixture of cell material and the enzyme; and
   (b) affinity extracting the enzyme from the mixture with an aqueous 2-phase extracting agent, one phase of which contains a triazine dyestuff bonded to an inert, water-soluble polymer.

2. Process according to claim 1, wherein the *Candida boidinii* cells, are frozen cells, suspended in an aqueous medium, containing potassium phosphate and/or potassium hydrogen phosphate, and left in suspension until an enzyme efflux of a maximum of approximately 90 to 75% (FDH-activity) has occurred.

3. Process according to claim 1, wherein the disintegrated cell mixture is heated and then cooled before being subjected to the affinity extraction.

4. Process according to claim 1 wherein there is used an aqueous 2-phase system with
   (a) polyethylene glycol or polypropylene glycol and
   (b) crude dextran, dextran, methylcellulose or Ficoll as phase former.

5. Process according to claim 4, wherein a salt is added to the phase containing the concentrated enzyme whereby the enzyme is conveyed into the other phase of the 2-phase system.

6. Process according to claim 5 wherein polyethylene glycol or polypropylene glycol is added to the phase into which the enzyme has been conveyed.

7. Process according to claim 5, wherein the enzyme is separated in a liquid medium free of phase formers and salts, and is then lyophilised in the presence of saccharose.

8. Process according to claim 5 which further comprises separating the enzyme from the other phase of the two phase system by ultra-filtration.

9. Process according to claim 1 wherein there is used as dyestuff Procion-red-HE3b bonded to polyethylene glycol or polypropylene glycol.

10. The process according to claim 1 wherein the enzyme is separated from the extracting agent.

11. Process according to claim 1 which further comprises separating the cells and cell debris from the mixture obtained by disintegrating the cells, prior to affinity extraction.

12. Process according to claim 1 which further comprises separating protein from the mixture obtained by disintegrating the cells, prior to affinity extraction.

13. Process for the purification and recovery of formate-dehydrogenase enzyme from *Candida boidinii*, which comprises;
   providing frozen cells of *Candida boidinii*;
   suspending the cells in an aqueous medium containing a salt selected from the group consisting of potassium phosphate, potassium hydrogen phosphate and mixture thereof;
   leaving the cells suspended in the solution until an enzyme efflux of a maximum of approximately 90 to 75 percent activity is achieved; and
   affinity extracting the enzyme from the solution with an aqueous 2-phase extracting agent, in one phase of which there is a concentrated triazine dyestuff bonded to an inert, water-soluble polymer.

14. The process of claim 13 wherein the enzyme is separated from the extracting agent.

* * * * *